US008821814B2

(12) United States Patent
Cho et al.

(10) Patent No.: US 8,821,814 B2
(45) Date of Patent: Sep. 2, 2014

(54) CARTRIDGE CONTAINING REAGENT, MICROFLUIDIC DEVICE INCLUDING THE CARTRIDGE, METHOD OF MANUFACTURING THE MICROFLUIDIC DEVICE, AND BIOCHEMICAL ANALYSIS METHOD USING THE MICROFLUIDIC DEVICE

(75) Inventors: Yoonkyoung Cho, Suwon-si (KR); Dogyoon Kim, Yongin-si (KR); Beomseok Lee, Hwaseong-si (KR); Jongmyeon Park, Seoul (KR); Hyunmin Kim, Gwangju-si (KR); Yangui Lee, Seoul (KR); Jong Gun Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 351 days.

(21) Appl. No.: 12/494,614

(22) Filed: Jun. 30, 2009

(65) Prior Publication Data

US 2010/0009431 A1 Jan. 14, 2010

(30) Foreign Application Priority Data

Jul. 10, 2008 (KR) ........................ 10-2008-0067206
Jun. 18, 2009 (KR) ........................ 10-2009-0054613

(51) Int. Cl.
*C12M 1/10* (2006.01)
*C12M 1/16* (2006.01)
*B01J 19/00* (2006.01)
*B01L 3/00* (2006.01)

(52) U.S. Cl.
USPC ............ 422/506; 422/68.1; 422/72; 422/500; 422/501; 422/507; 422/538; 422/261; 422/270; 435/287.3; 435/287.9; 435/288.2; 435/288.5; 435/288.7; 435/289.1

(58) Field of Classification Search
USPC .......... 422/68.1, 72, 500, 501, 506, 507, 538, 422/261, 270; 435/287.3, 287.9, 288.2, 435/288.5, 288.7, 289.1
See application file for complete search history.

(56) References Cited

U.S. PATENT DOCUMENTS

| | | | | |
|---|---|---|---|---|
| 6,740,530 | B1 * | 5/2004 | Bruce et al. | 436/180 |
| 2003/0161763 | A1 * | 8/2003 | Erden et al. | 422/99 |
| 2005/0112023 | A1 | 5/2005 | Liang | |
| 2006/0257992 | A1 * | 11/2006 | McDevitt et al. | 435/287.2 |

FOREIGN PATENT DOCUMENTS

| | | | |
|---|---|---|---|
| JP | 2007-127495 | A | 5/2007 |
| JP | 2007-278741 | A | 10/2007 |
| JP | 2008-064753 | A | 3/2008 |
| WO | 2006/137785 | A1 | 12/2006 |

OTHER PUBLICATIONS

State Intellectual Property Office of P.R. China, Communication dated Feb. 28, 2013, issued in counterpart Chinese Patent Application No. 200980126967.1.
Communication from the Taiwanese Patent Office dated May 24, 2013, in a counterpart Taiwanese application No. 098123316.

* cited by examiner

*Primary Examiner* — Jill Warden
*Assistant Examiner* — Timothy G Kingan
(74) *Attorney, Agent, or Firm* — Sughrue Mion, PLLC

(57) ABSTRACT

A microfluidic device including a platform and a cartridge is disclosed. The platform includes a chamber containing a fluid. The reagent cartridge is mounted to the platform. and contains a solid reagent for detecting material contained in the fluid.

35 Claims, 12 Drawing Sheets

CARTRIDGE CONTAINING REAGENT, MICROFLUIDIC DEVICE INCLUDING THE CARTRIDGE, METHOD OF MANUFACTURING THE MICROFLUIDIC DEVICE, AND BIOCHEMICAL ANALYSIS METHOD USING THE MICROFLUIDIC DEVICE

CROSS-REFERENCE TO RELATED PATENT APPLICATIONS

This application claims the benefit of Korean Patent Application No. 10-2008-0067206, filed on Jul. 10, 2008, and Korean Patent Application No. 10-2009-0054613, filed on Jun. 18, 2009, in the Korean Intellectual Property Office, the disclosures of which are incorporated herein in their entirety by reference.

BACKGROUND

1. Field

One or more embodiments of the present invention relate to a cartridge containing a reagent, a microfluidic device including the cartridge, a method of manufacturing the microfluidic device, and a biochemical analysis method using the microfluidic device.

2. Description of the Related Art

Various methods of analyzing a sample have been developed to, for example, monitor environments, examine food, or diagnose the medical condition of a patient. However, these methods require many manual operations and the use of various devices. To perform an assay or test according to a predetermined protocol, those skilled in the manual operations repeatedly perform various processes including loading of a reagent, mixing, isolating and transporting, reacting, and centrifuging. However, such repeated manual processes result in erroneous results due to "human error."

To perform tests quickly, skilled clinical pathologists are needed. However, it is hard for even a skilled clinical pathologist to perform various tests at the same time. Even more serious, rapid test results are necessary for timely treatment of emergency patients. Accordingly, analytical equipment enabling the simultaneous, rapid and accurate performing of pathological examinations for given circumstances is desired.

Conventional pathological assays are performed with large and expensive pieces of automated equipment which also require a considerable amount of a sample, such as blood. Moreover, it usually takes days to weeks to obtain results of the pathological assays.

In a small-sized and automated equipment, it is possible to analyze a sample of one patient or, if necessary, plural samples taken from one patient or different patients. An example of such a system involves the use of a microfluidic device, wherein a fluid biological sample such as blood is loaded into a disk-shaped microfluidic device and the disk-shaped microfluidic device is rotated, and then serum can be isolated from blood due to the centrifugal force. The isolated serum is mixed with a predetermined amount of a diluent or a buffer solution and the mixture then flows into a plurality of reaction chambers in the disk-shaped microfluidic device. The reaction chambers usually contain reagents that are loaded prior to allowing the mixture to flow therein. Reagents used may differ according to various purposes. When the serum interacts with different reagents, colors of the mixture may change. The change in color is used to determine if the sample contains a certain component.

However, storing a reagent in a liquid state is difficult. U.S. Pat. No. 5,776,563 discloses a system in which a lyophilized reagent is stored and, when blood analysis is performed, a certain amount of the lyophilized reagent is loaded into reaction chambers of a disk-shaped microfluidic device.

SUMMARY

One or more embodiments include a cartridge containing a reagent, a microfluidic device including the cartridge, a method of manufacturing the microfluidic device, and a biochemical analysis method using the microfluidic device.

Additional aspects and/or advantages will be set forth in part in the description which follows and, in part, will be apparent from the description, or may be learned by practice of the invention.

To achieve the above and/or other aspects and advantages, one or more embodiments may include a microfluidic device comprising: a platform including a chamber containing a fluid; and a reagent cartridge mounted to the platform, the reagent cartridge comprising a closed first end, a closed second end, a sidewall connecting the first end and the second end, an opening formed in the sidewall, and a well containing a solid reagent for detecting a material contained in the fluid.

According to an embodiment of the present inventive concept, the solid reagent is a lyophilized solid reagent, that is soluble in the fluid.

According to an embodiment of the present inventive concept, the microfluidic device may include at least two reagent cartridges containing the same or different lyophilized reagents.

According to an embodiment of the present inventive concept, the reagent cartridge may include a plurality of compartments or wells each containing a different reagent from the other wells.

According to an embodiment, the cartridge includes a body including a closed first end, a closed second end, a sidewall connecting the first and second ends, an opening formed in the sidewall, and a well accessible through the opening; and a solid reagent contained in the well.

According to an embodiment of the present inventive concept, the platform includes at least one detection chamber in which the reagent cartridge is mounted. The detection chamber may include a mounting portion for accommodating the reagent cartridge and at least part of the detection chamber is made of a transparent material.

The reagent cartridge may be mounted in such a way that the opening of the reagent cartridge faces the detection portion so that the fluid flowing into the detection chamber can be introduced into the reagent cartridge. The fluid introduced into the detection chamber and/or reagent cartridge contacts and dissolves the reagent contained in the reagent cartridge.

According to an embodiment of the present inventive concept, the platform includes: a sample chamber to accommodate the sample; a diluent chamber to accommodate a diluent; a detection chamber to accommodate the reagent cartridge; and a valve for controlling the flow of the fluid disposed at at least one point between said chambers.

According to an embodiment of the present inventive concept, the valve may be controlled according to pressure of the fluid. The pressure may be generated when the microfluidic device rotates.

According to an embodiment of the present inventive concept, the valve may be formed of a valve forming material that opens by electromagnetic radiation energy. The valve forming material may be selected from a phase transition material and a thermoplastic resin, wherein the phase of the phase transition material or the thermoplastic resin changes by electromagnetic radiation energy.

According to an embodiment of the present inventive concept, the valve forming material may include micro heat-dissipating particles which are dispersed in the phase transition material, and absorb the electromagnetic radiation energy and generate heat.

According to an embodiment of the present inventive concept, the microfluidic device may further include a container coupled to the platform and providing the diluent to the diluent chamber.

According to an embodiment of the present inventive concept, the reagent may include at least one reagent selected from the group consisting of reagents for detecting serum, aspartate aminotransferase (AST), albumin (ALB), alkaline phosphatase (ALP), alanine aminotransferase (ALT), amylase (AMY), blood urea nitrogen (BUN), calcium ($Ca^{++}$), total cholesterol (CHOL), creatine kinase (CK), chloride ($Cl^-$), creatinine (CREA), direct bilirubin (D-BIL), gamma glutamyl transferase (GGT), glucose (GLU), high-density lipoprotein cholesterol (HDL), potassium ($K^+$), lactate dehydrogenase (LDH), low-density lipoprotein cholesterol (LDL), magnesium (Mg), phosphorus (PHOS), sodium ($Na^+$), total carbon dioxide ($TCO_2$), total bilirubin (T-BIL), triglycerides (TRIG), uric acid (UA), and total protein (TP).

According to an embodiment of the present inventive concept, the lyophilized reagent may include a filler. The filler may be a water-dissolvable material which includes at least one material selected from the group consisting of bovine serum albumin (BSA), polyethylene glycol (PEG), dextran, mannitol, polyalcohol, myo-inositol, an citric acid, ethylene diamine tetra acetic acid disodium salt (EDTA2Na), and polyoxyethylene glycol dodecyl ether (BRIJ-35).

According to an embodiment of the present inventive concept, the solid reagent may include a surfactant. The surfactant may include at least one material selected from the group consisting of polyoxyethylene, lauryl ether, octoxynol, polyethylene alkyl alcohol, nonylphenol polyethylene glycol ether; ethylene oxide, ethoxylated tridecyl alcohol, polyoxyethylene nonylphenyl ether phosphate sodium salt, and sodium dodecyl sulfate.

At least a portion of a shape of the solid reagent may be complementary to at least a portion of the shape of the at least one reagent cartridge.

To achieve the above and/or other aspects and advantages, one or more embodiments of the present invention may include a cartridge including: a body; at least one reagent compartment formed in the body; and a solid reagent contained in the reagent compartment, in which the body has a sidewall, a first end, and a second end, and an opening formed in the sidewall.

The cartridge may include at least two reagent compartments each containing a different reagent.

According to an embodiment of the present inventive concept, the solid reagent may be a lyophilized solid reagent. At least one portion of the shape of the lyophilized solid reagent is identical to at least one portion of the shape of the at least one reagent compartment.

To achieve the above and/or other aspects and advantages, one or more embodiments of the present invention may include a method of manufacturing a microfluidic device, the method including: providing a platform having a chamber containing a fluid; providing a reagent cartridge containing an unit usage amount of a solid reagent; and mounting the reagent cartridge on the platform. The solid reagent may be produced by lyophilization of a liquid reagent.

The lyophilizing of the loaded reagent may include: loading a first reagent in a liquid state and a second reagent in a liquid state into each of individual reagent compartments (or wells) of the reagent cartridge, respectively; and lyophilizing the liquid first reagent and the liquid second reagent.

To achieve the above and/or other aspects and advantages, one or more embodiments of the present invention may include a method of analyzing a sample, the method including: providing a microfluidic device which includes chambers accommodating a fluid; mounting a reagent cartridge into one of the chambers ("a first chamber"), the reagent cartridge containing a reagent; loading the fluid to one of the chambers ("a second chamber"); allowing the fluid to be in contact with the reagent in the first chamber; and determining whether the reagent is reacted with the fluid.

According to an embodiment of the present inventive concept, at least one portion of the shape of the lyophilized first reagent is complementary to at least one portion of the shape of the first and second reagent cartridge, and at least one portion of the shape of the lyophilized second reagent is identical to at least one portion of the shape of the second reagent cartridge.

The reagent cartridge may have at least one structure that supports holding or retention of the lyophilized reagent therein. The structure may be formed inside the wells of the reagent cartridge and may have shape of protrusion. The protrusion structure may be formed at the opening.

The detection chamber may have a structure to retain the reagent within the detection chamber.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION

Figure 1:
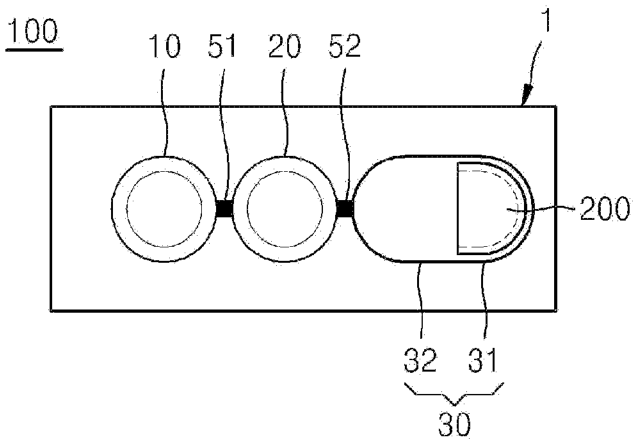
FIG. 1 is a plan view of a microfluidic device according to an embodiment of the present inventive concept.

Reference will now be made in detail to embodiments, examples of which are illustrated in the accompanying drawings, wherein like reference numerals refer to the like elements throughout. In this regard, the present invention may be embodied in many different forms and should not be construed as being limited to the embodiments set forth herein. Accordingly, embodiments are merely described below, by referring to the figures, to explain aspects of the present invention.

Figure 2:
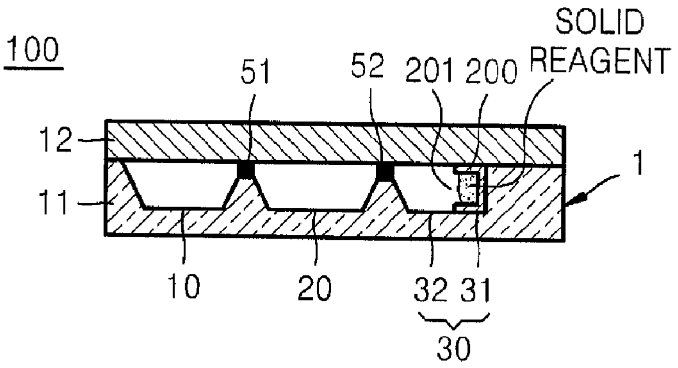
FIG. 2 is a cross-sectional view of the microfluidic device of FIG. 1, which is illustrated as a two-layered microfluidic device according to an embodiment of the present inventive concept.
Figure 3:
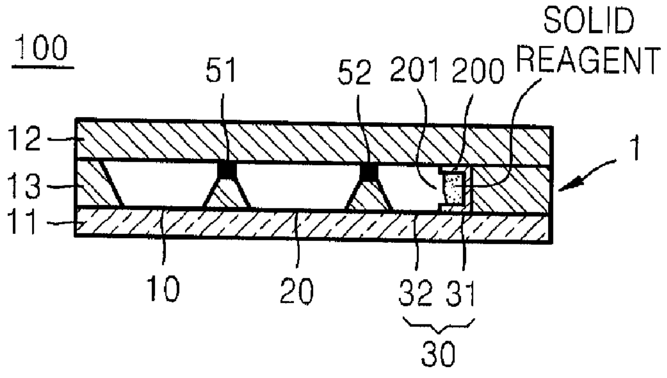
FIG. 3 is a cross-sectional view of the microfluidic device of FIG. 1, which is illustrated as a three-layered microfluidic device according to another embodiment of the present inventive concept.

FIG. 1 is a plan view of a microfluidic device 100 according to an embodiment of the present inventive concept, and FIGS. 2 and 3 are cross-sectional views of the microfluidic device 100 of FIG. 1, according to two different embodiments of the present inventive concept.

Referring to FIGS. 1 and 2, the microfluidic device 100 has a platform 1 including a chamber for storing a fluid and a channel through which the fluid flows. The platform 1 may be formed of a plastic material that can be easily molded and is biologically inactive. Examples of the plastic material include acryl, polymethyl methacrylate (PMMA), and a cyclic olefin copolymer (COC). However, a material for forming the platform 1 is not limited to those materials listed above and can be any material that has chemical and biological stability, optical transparency, and mechanical processability. The platform 1 may have, as illustrated in FIG. 2, a two-layer structure including a bottom plate 11 and a top plate 12. The platform 1 can also have, as illustrated in FIG. 3, a three-layered structure including a bottom plate 11, a top plate 12, and a partitioning (or intermediate) plate 13 disposed between the bottom plate 11 and the top plate 12. The partitioning plate 13 defines a portion for storing a fluid and a channel through which the fluid flows. The bottom plate 11, the top plate 12, and the partitioning plate 13 can be bonded together by using various materials, such as double-sided tape or an adhesive, or by fusing using ultrasonic waves. The platform 1 can also be formed of other structures.

Hereinafter, a structure for a blood test formed in the platform 1 will be described in detail. A sample chamber 10 is formed in the platform 1. The sample chamber 10 contains a sample, such as blood or serum. A diluent chamber 20 contains a diluent that is used to dilute the sample to a desired concentration suitable for examinations. The diluent may be, for example, a buffer or distilled water (DI). A detection chamber 30 is the chamber where the sample mixed with the diluent is brought in contact with a reagent which can interact with a certain (or target) component in the sample, and the interaction can be detected by various means including color change detection. The detection chamber 30 includes a reagent cartridge 200 containing a reagent.

The sample chamber 10 is connected to and in fluid communication with the diluent chamber 20. The diluent chamber 20 is connected to and in fluid communication with the detection chamber 30. Herein, the term "connection" between chambers and/or channels are used to mean these chambers and/or channels are in fluid communication with each other and the fluid flow may be controlled by a valve located on the flow passage, for example channels. For example, a valve 51 is located between the sample chamber 10 and the diluent chamber 20 to control flow of a fluid between the sample chamber 10 and the diluent chamber 20. A valve 52 is located between the diluent sample 20 and the detection chamber 30 to control flow of a fluid between the diluent sample 20 and the detection chamber 30. Although not illustrated, the platform 1 may include: inlets for loading the sample, the diluent, and the reagent; and an air vent for discharging air.

Figure 4:
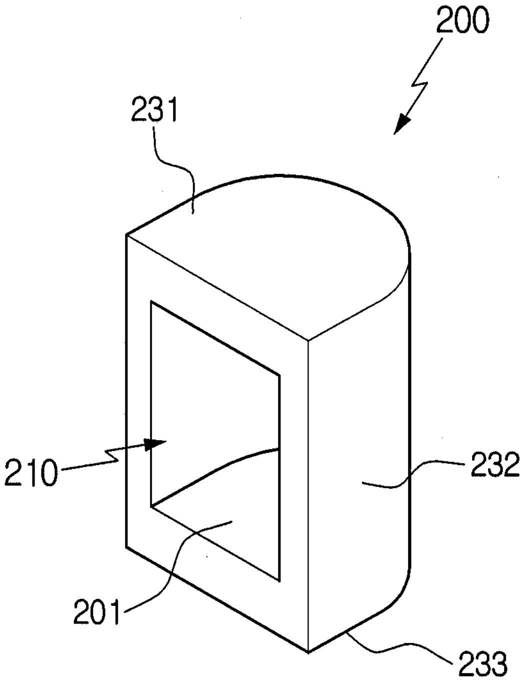
FIG. 4 is a perspective view of a reagent cartridge containing a reagent, according to an embodiment of the present inventive concept.

FIG. 4 is a perspective view of a reagent cartridge 200 containing a reagent, according to an embodiment of the present inventive concept.

Figure 13A:
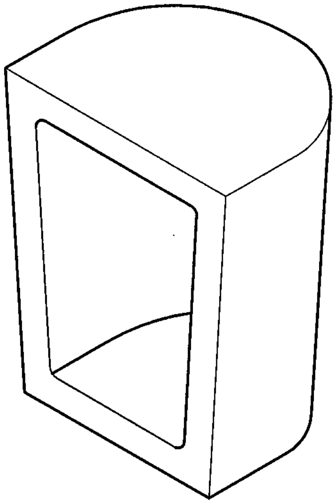
FIGS. 13A through 13K depicts various structures of the reagent cartridges as well as a plan views of the device containing the reagent cartridges.

Referring to FIG. 4, the reagent cartridge 200 includes a body which comprises a first end 231, a second end 233 and, a sidewall 232 connecting the first end 231 and the second end 233. The sidewall may have a partial cylindrical shape as shown in FIG. 4. The surface area of the first end and the surface area of the second end may be the same (e.g., FIG. 4) or different (FIG. 13A). The structure of the reagent cartridge is not critical and may be determined depending on the feasibility or easiness of fabricating them.

The body of the reagent cartridge 200 further includes a reagent compartment (or reagent well) 201 containing a reagent. An opening 210 is formed in the sidewall 232 to allow access to the reagent contained in the reagent compartment 201. Because the first end 231, the second end 233, and the sidewall 232 are all closed, the reagent contained in the reagent compartment 201 is accessible only through the opening 210 in the embodiment illustrated in FIG. 4.

The terms "reagent compartment" and "reagent well" are interchangeably used throughout the application. The reagent well 201 may have various internal shapes. In addition, the reagent well 201 may have markings indicating the volume of the reagent contained therein. In an embodiment of the present inventive concept, the reagent cartridge 200 may be cased, installed, or fitted in a chamber ("a reagent cartridge housing chamber" or "detection chamber") 30 The fitting of the reagent cartridge 200 in the chamber 30 may be done loosely (or snuggly) or tightly. When plural reagent housing chambers are provided and respective of them is mounted with a different reagent-containing reagent cartridge, at least one, for example, the last one of the chambers may be used to detect a reaction between the sample (a component to be tested and expected to be contained in the sample) and the reagent(s).

The reagent well may have at least one structure to support holding the solid lyophilized reagent therein. For example, as shown in FIG. 13H, FIG. 13I, FIG. 13J, and FIG. 13K the reagent well may be provide with protrusion(s) 211*a*, 211*b*, 211*c*, or 211*d* that support(s) holding of the reagent in the well. The shape and location of the protrusion is not limited as long as it enhance the holding of the lyophilized reagent in the well.

In a sample analysis process which will be described later, light is to be projected into the detection chamber 30. Thus, at least a portion of the platform 1 in which the detection chamber 30 is located may be formed of a material that transmits light. If the reagent cartridge 200 is formed of a material that transmits light, the reagent cartridge 200 may be manufactured in such a way that the reagent cartridge 200 can loosely or tightly fit into the chamber 30. In FIG. 1, a projected area of the reagent cartridge 200 is smaller than a projected area of the detection chamber 30. If the projected area of the reagent cartridge 200 is smaller than the projected area of the detection chamber 30, light is projected into a portion of the detection chamber 30 in which the reagent cartridge 200 is not located and high light transmittance and accurate detection results can be obtained. If the reagent is a reagent that is susceptible to light, the reagent should not be exposed to light. To this end, the reagent cartridge 200 may be formed of a material that does not transmit light.

Accordingly, as illustrated in FIG. 1, the detection chamber 30 includes a mounting portion 31 for housing the reagent cartridge 200 and a detection portion 32 for detecting the interaction between the reagent and the target component in the sample. At least part of the detection chamber 30, such as the detection portion 32, allows light to be transmitted. The reagent cartridge 200 may be mounted in the mounting portion 31 in such a way that the opening 210 of the reagent cartridge 200 faces the detection portion 32 of the detection chamber. In an embodiment of the present inventive concept, the reagent cartridge 200 may be mounted in such a way that the opening 210 faces a path of a fluid flowing into the detection chamber 30, that is, the valve 52. Thus, upon the introduction of the sample mixed with a diluent into the detection chamber from the diluent chamber (20 in FIG. 1), the sample contacts and dissolves the lyophilized reagent in the reagent cartridge 200, which is housed in the detection chamber (30 in FIG. 1).

Figure 13B:
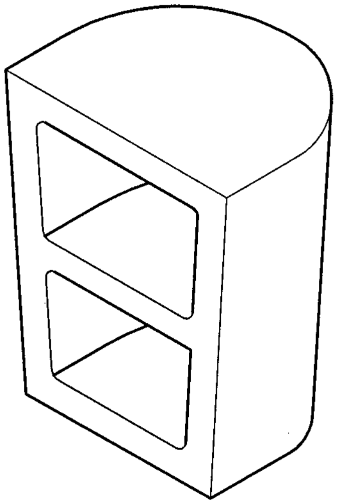
Figure 13C:
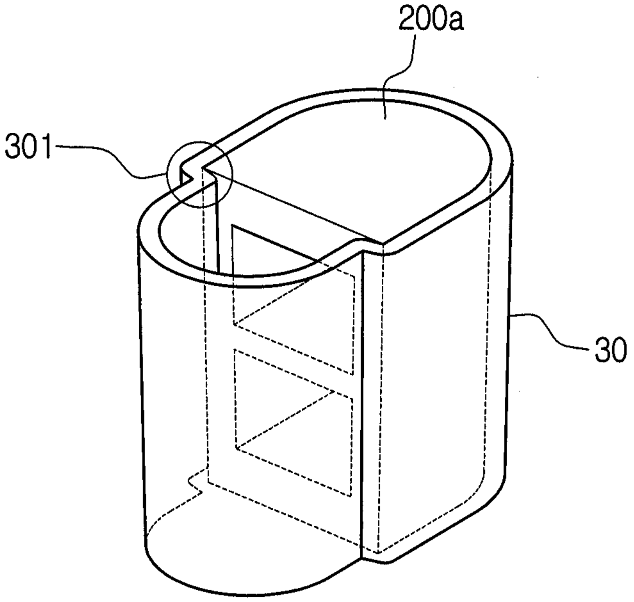
Figure 13D:
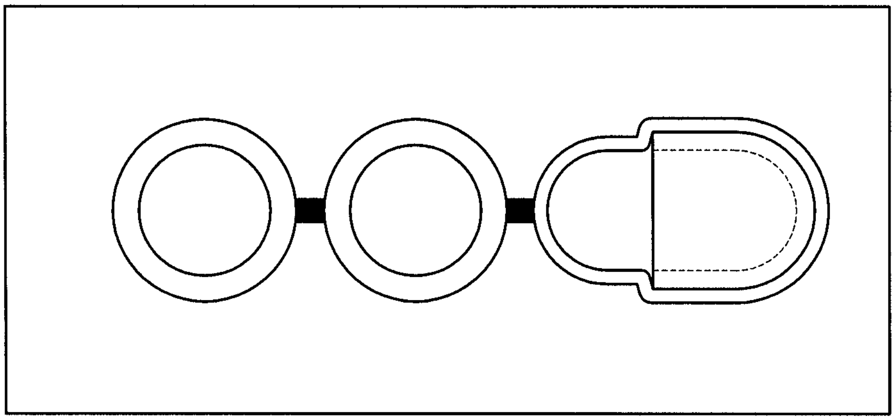
Figure 13E:
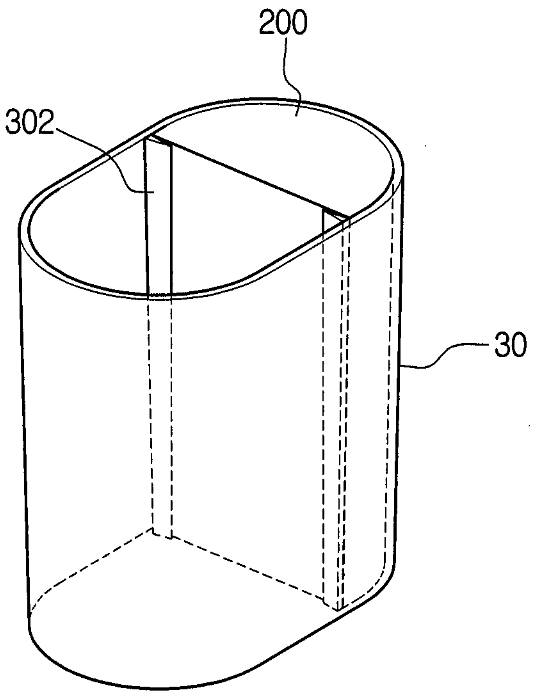
Figure 13F:
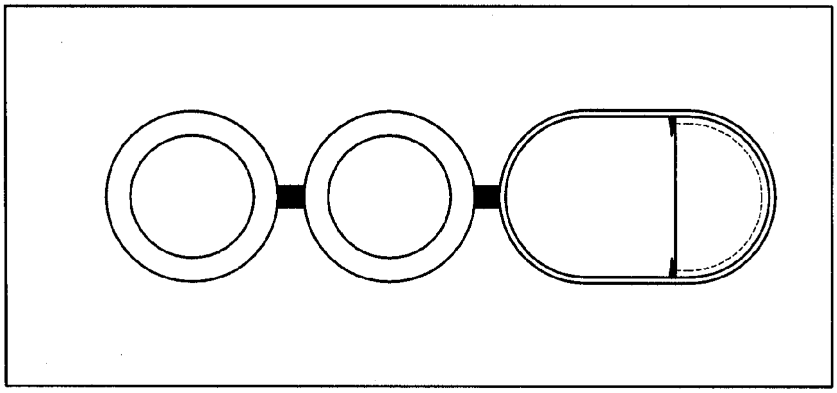

The detection chamber may have a configuration which prevents free moving of the reagent cartridge in the chamber. For example, as shown in FIG. 13C, the detection chamber 30 may have an indent 301 to prevent the reagent cartridge 200*a* from freely moving from its original housing place. FIG. 13D shows a plan view of a microfluidic device having such detection chamber. FIG. 13E shows another exemplary embodiment of such structure wherein the detection chamber 30 has protrusions 302 in the inside wall thereof so that it can secure the holding of the reaction cartridge. FIG. 13F shows a plan view of such embodiment of FIG. 13E. While FIGS. 13C, 13D, 13E, and FIG. 13F show a particular configuration, the present inventive concept is not limited thereto.

Various types of microfluidic valves can be used as the valves 51 and 52. For example, the valves 51 and 52 may be valves that open or close according to a flow rate of the fluid, that is, valves that passively open when applied pressure that is generated due to flow of the fluid reaches or exceeds a predetermined level. Examples of such valves include a capillary valve using a micro channel structure, a siphon valve, and a hydrophobic valve which has a surface treated with a hydrophobic material. Such valves may be controlled according to a rotation rate of a microfluidic device. That is, as the rotation rate of the microfluidic device is increased, more pressure is applied to a fluid in the microfluidic device, and if the applied pressure reaches or exceeds a predetermined level, the valves open and the fluid flows.

In addition, the valves 51 and 52 can also be valves that are actively operated when an operation signal is transmitted and an operating power is externally provided. In the current embodiment, the valves 51 and 52 are values that operate when a valve forming material absorbs electromagnetic radiation emitted from an external source. The valves 51 and 52 are so called “normally closed” valves that block the flow of the fluid before electromagnetic radiation energy is absorbed.

The valve forming material may be a thermoplastic resin, such as a COC, PMMA, polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), or polyvinylidene fluoride (PVDF).

The valve forming material can also be a phase transition material that exists in a solid state at room temperature. The phase transition material is loaded when in a liquid state into channels, and then solidified to close the channels. The phase transition material may be wax. When heated, wax melts into a liquid and the volume thereof increases. The wax may be, for example, paraffin wax, microcrystalline wax, synthetic wax, or natural wax. The phase transition material may be gel or a thermoplastic resin. Examples of the gel may include polyacrylamides, polyacrylates, polymethacrylates, and polyvinylamides.

In the phase transition material, a plurality of micro heat-dissipating particles that absorb electromagnetic radiation energy and dissipate thermal energy may be dispersed. The diameter of the micro heat-dissipating particles may be about 1 nm to about 100 μm so that the micro heat-dissipating particles freely pass through micro fluid channels having a depth of about 0.1 mm and a width of about 1 mm. When electromagnetic radiation energy of, for example, a laser ray, is supplied, the temperature of the micro heat-dissipating particles increases significantly, and thus, the micro heat-dissipating particles dissipate thermal energy and become uniformly dispersed in the wax. Each micro heat-dissipating particle having the characteristics described above includes a core including metal and a hydrophobic shell. For example, each micro heat-dissipating particle may include a core formed of Fe, and a shell layer surrounding the core. The shell layer may be formed of surfactant. The surfactant molecules may be bonded to the Fe core. The micro heat-dissipating particles may be stored in a state of being dispersed in carrier oil. The carrier oil may be hydrophobic to uniformly disperse micro heat-dissipating particles having a hydrophobic surface structure. The carrier oil in which the micro heat-dissipating particles are dispersed is mixed with a molten phase transition material, and the obtained mixture is loaded between chambers and solidified, thereby blocking the flow of the fluid between the chambers.

The micro heat-dissipating particles may be, in addition to the polymer particles described above, quantum dots or magnetic beads. The micro heat-dissipating particles can also be micro particles of metal oxide, such as $Al_2O_3$, $TiO_2$, $Ta_2O_3$, $Fe_2O_3$, $Fe_3O_4$ or, $HfO_2$. However, the inclusion of the micro heat-dissipating particles in the valves 51 and 52 is optional. For example, the valves 51 and 52 can be formed of only a phase transition material. A portion of the platform 1 corresponding to the valves 51 and 52 may be transparent to electromagnetic radiation irradiated from an external source so that the electromagnetic radiation is incident on the valves 51 and 52.

In a microfluidic analysis, it is difficult to load an accurate amount of the lyophilized solid reagent into the detection chamber 30, because the reagent is likely to be lyophilized into non-uniform sizes of beads. Even if the lyophilized beads have a uniform size, the lyophilized beads may be easily broken. In addition, when the reagent beads are loaded into the detection chamber 30 while being exposed to humidity, the performance of the reagent may be degraded. According to the current embodiment, a unit usage amount of the reagent is loaded into the well of the reagent cartridge 200, which is then lyophilized. Thus produced lyophilized reagent may have a solid cake appearance and moisture content. The reagent cartridge 200 which contains a unit usage amount of a solid lyophilized reagent, may be mounted into the microfluidic device. As the reagent is in-situ lyophilized in the well of the reagent cartridge, at least one portion of the shape of the solid lyophilized reagent is complementary to a portion of the internal shape of the reagent cartridge 200, specifically, at least one portion of the internal shape of the reagent well 201. A method of in-situ lyophilization of the reagent will now be described in detail.

First, the reagent in a liquid state is loaded into the reagent well 201 of the reagent cartridge 200. To decrease the volume of the reagent loaded into the reagent well 201, the liquid reagent may have a higher concentration or titer than that suitable for the contemplated tests.

The reagent for a blood test may be a reagent for detecting, for example, serum, aspartate aminotransferase (AST), albumin (ALB), alkaline phosphatase (ALP), alanine aminotransferase (ALT), amylase (AMY), blood urea nitrogen (BUN), calcium ($Ca^{++}$), total cholesterol (CHOL), creatine kinase (CK), chloride ($Cl^-$), creatinine (CREA), direct bilirubin (D-BIL), gamma glutamyl transferase (GGT), glucose (GLU), high-density lipoprotein cholesterol (HDL), potassium ($K^+$), lactate dehydrogenase (LDH), low-density lipoprotein cholesterol (LDL), magnesium (Mg), phosphorus (PHOS), sodium ($Na^+$), total carbon dioxide ($TCO_2$), total bilirubin (T-BIL), triglycerides (TRIG), uric acid (UA), or total protein (TP). In addition, it would be obvious to one of ordinary skill in the art that the microfluidic device according to the present invention can also be used to analyze various other samples that can be taken from a human body or any organism.

An additive may be added to the liquid reagent. For example, to increase dispersibility of the resultant lyophilized reagent, when it is in contact with a sample mixed in a diluent, a filler that imparts or increases porosity of the lyophilized reagent may be used. Therefore, when a sample diluent (i.e., a sample mixed with a diluent) is loaded into the detection chamber 30, the lyophilized reagent can be easily dissolved. For example, the filler may include at least one material selected from the group consisting of bovine serum albumin (BSA), polyethylene glycol (PEG), dextran, mannitol, polyalcohol, myo-inositol, an citric acid, ethylene diamine tetra acetic acid disodium salt (EDTA2Na), and polyoxyethylene glycol dodecyl ether (BRIJ-35). The type and amount of the filler may differ according to the type of the reagent.

A surfactant may be added to the liquid reagent. For example, the surfactant may include at least one material selected from the group consisting of polyoxyethylene, lauryl ether, octoxynol, polyethylene alkyl alcohol, nonylphenol polyethylene glycol ether, ethylene oxide, ethoxylated tridecyl alcohol, polyoxyethylene nonylphenyl ether phosphate sodium salt, and sodium dodecyl sulfate. The amount and type of the surfactant may differ according to the type of the reagent.

A plurality of reagent cartridges 200 containing the liquid reagent are loaded into a lyophilizing device and then an appropriate method is employed according to a lyophilizing program. In this regard, to easily identify the amount or kind of reagent, different reagents may be loaded into different color reagent cartridges 200, or a recognizable sign for identifying reagents may be attached to the reagent cartridge 200. Examples of the recognizable sign may include a marker and a barcode.

The lyophilizing program may differ according to the amount and type of liquid reagent. The lyophilizing method includes a freezing process whereby water included in a material is frozen and a drying process whereby the frozen water is removed. In general, the drying process uses a sublimating process whereby frozen water is directly changed into a vapor. However, the entire drying process does not necessarily require sublimation, that is, only a part of the drying process may require sublimation. To perform the sublimating process, the pressure in the drying process may be adjusted to be equal to or lower than the triple point of water (about 6 mbar or about 4.6 Torr). However, there is no need to maintain a predetermined pressure. In the drying process, the temperature may be changed. For example, after the freezing process is completely performed, the temperature may be gradually increased.

Through the processes described above, the lyophilized solid reagent has the shape at least partially complementary to at least one portion of the reagent cartridge 200, specifically, at least one portion of the inner configuration of the reagent well 201. In the lyophilizing process, the reagent cartridge 200 is inserted into a lyophilizer in such a way that the opening 210 of the reagent well 201 faces upward. Accordingly, the shape of the lyophilized reagent may be complementary to the shape of the portion of the reagent well 201, which is opposite to the opening (210 in FIG. 4).

As described above, since the reagent is loaded when in a liquid state into the reagent cartridge 200, the amount of the reagent can be accurately controlled. In addition, since the lyophilizing process is performed after the liquid reagent is loaded into the reagent cartridge 200, it is possible to mass produce the reagent cartridges 200 containing the lyophilized reagent for analyzing the same target material.

The term "unit usage amount" of a reagent is used herein to mean an amount of a reagent that is used for a single test and produces a desired or required amount and concentration of the reagent with or without a dilution with a diluent after the reagent cartridge containing an unit usage amount of the reagent is mounted in a microfluidic device for an assay.

The reagent cartridge 200 containing a unit usage amount of the lyophilized reagent prepared as described above is mounted in the mounting portion 31 of the detection chamber 30 formed in the bottom plate 11, or in the detection chamber 30 defined by the bottom plate 11 and the partitioning plate 13. Then, the top plate 12 is coupled to the bottom plate 11 or the partitioning plate 13, thereby completing the manufacture of the microfluidic device according to an embodiment of the present inventive concept. To fix the reagent cartridge 200 mounted in the detection chamber 30, the reagent cartridge 200 may be coupled to the detection chamber 30 by attaching or interference-fitting. In addition, various fixing methods can be used to fix the reagent cartridge 200.

Figure 6:
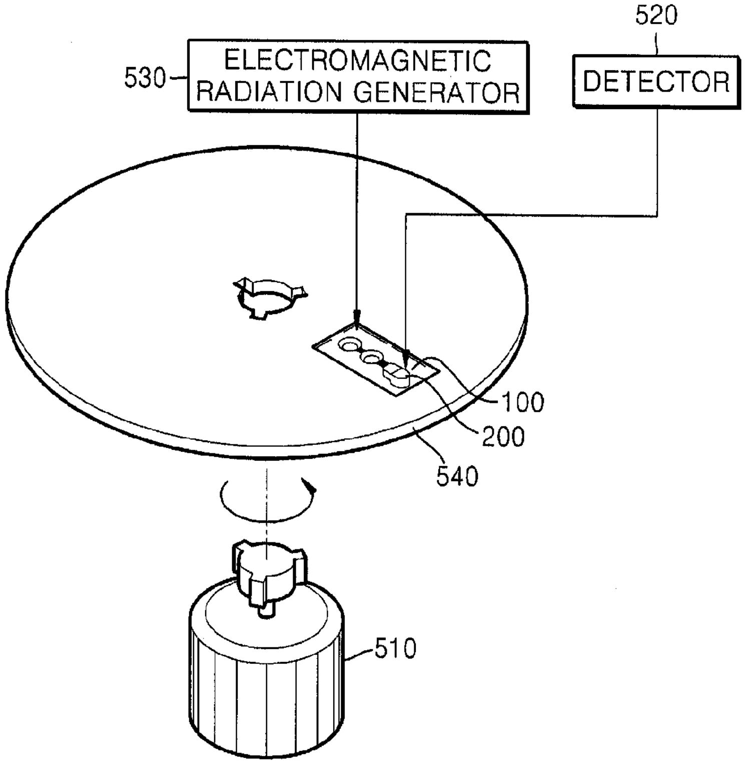
FIG. 6 is a schematic view of an analyzer using the microfluidic device of FIG. 1.

FIG. 6 is a schematic view of an analyzer using the microfluidic device 100 of FIG. 1. Referring to FIG. 6, a rotary driving unit 510 rotates the microfluidic device 100 and mixes the sample, the diluent, and the reagent by a centrifugal force. The rotary driving unit 510 moves the microfluidic device 100 to a predetermined position so that the detection chamber 30 faces a detector 520. Although the rotary driving unit 510 is not entirely shown, the rotary driving unit 510 may further include a motor drive device (not shown) for controlling an angular position of the microfluidic device 100. The motor drive device may use a step motor or a direct-current motor. The detector 520 detects, for example, optical characteristics, such as fluorescent, luminescent, and/or absorbent characteristics, of a material to be detected. An electromagnetic radiation generator 530 is used to operate the valves 51 and 52, and emits, for example, a laser beam.

A method of analyzing the sample will now be described in detail. The diluent, such as a buffer or distilled water, is loaded into the diluent chamber 20 of the microfluidic device 100, and then, the sample, such as blood taken from a subject to be analyzed or serum separated from the blood, is loaded into the sample chamber 10.

Figure 5:
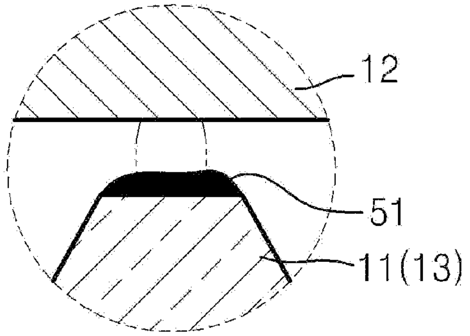
FIG. 5 is a sectional view of a channel that opens by a valve.

Then, the microfluidic device 100 is installed in the analyzer illustrated in FIG. 6. If the microfluidic device 100 is chip-shaped, the microfluidic device 100 cannot be directly mounted on the rotary driving unit 510. In this case, the microfluidic device 100 is inserted into an adaptor 540 and the adaptor 540 is mounted on the rotary driving unit 510. In this regard, since a fluid flows from the sample chamber 10 to the detection chamber 30, the microfluidic device 100 may be inserted in such a way that the sample chamber 10 is positioned closer to a rotary center of the adaptor 540 than the detection chamber 30. The rotary driving unit 510 rotates the microfluidic device 100 so that the valve 51 faces the electromagnetic radiation generator 530. When electromagnetic radiation is irradiated on the valve 51, a material that forms the valve 51 melts due to electromagnetic radiation energy and a channel between the sample chamber 10 and the diluent chamber 20 is opened as illustrated in FIG. 5. The sample flows to the diluent chamber 20 by a centrifugal force. The rotary driving unit 510 moves the microfluidic device 100 in a reciprocal motion to mix the sample with the diluent to form a sample diluent. The term "sample diluent" used throughout the application indicates a mixture of a sample and a diluent. Then, electromagnetic radiation is irradiated on the valve 52 to open a channel between the diluent chamber 20 and the detection chamber 30 and the sample diluent is loaded into the detection chamber 30. As a result, the lyophilized reagent contained in the reagent cartridge 200 is mixed with the sample diluent and melts. To dissolve the lyophilized reagent by mixing with the sample diluent, the rotary driving unit 510 may shake the microfluidic device 100 to the left and right a few times. As a result, a reagent mixture is formed in the detection chamber 30.

Then, the detection chamber 30 is moved to face the detector 520 so as to identify whether a material to be detected is present in the reagent mixture in the detection chamber 30, and to measure the amount of the material to be detected, thereby completing the sample analysis.

The reagent may be a mixture of two more reagents which can be used together for a desired reaction. If such coexistence may degrade or denature the activity of the reagent(s), like the case of an enzyme and a substrate, a reagent cartridge having two or more wells may be used to house such reagents that will be mixed together, when a sample diluent are brought to contact them in a detection chamber. Examples of such a reagent include a reagent for detecting alkaline phosphatase (ALP), a reagent for detecting alanine aminotransferase (ALT), a reagent for detecting high-density lipoprotein cholesterol (HDL), and a reagent for detecting low-density lipoprotein cholesterol (LDL). Specifically, in the case of the reagent for detecting ALP, p-nitrophenolphosphate (PNPP) functioning as a substrate is unstable when the pH is 10 or higher, and aminomethanpropanol (AMP) and diethanolamine (DEA) each functioning as a buffer that is necessary in a reaction system has a pH of 11-11.5. Therefore, the substrate and the buffer need to be separately lyophilized and stored.

In the case of the reagent for detecting AMY, NaCl is used. However, NaCl is difficult to lyophilize due to its strong deliquescent characteristics. Even when NaCl is lyophilized, the lyophilized NaCl immediately absorbs humidity and the shape thereof is changed, and titer of the reagent may be degraded. Therefore, NaCl needs to be separated from a substrate.

Figure 7:
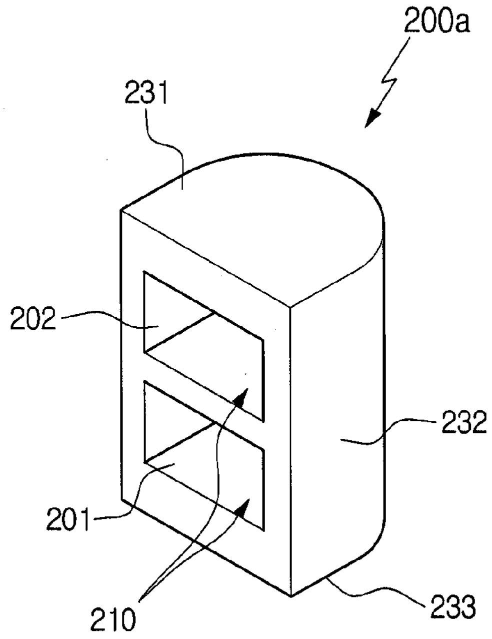
FIG. 7 is a perspective view of a cartridge containing a reagent, according to another embodiment of the present inventive concept.

Accordingly, as illustrated in FIG. 7, the reagent cartridge 200*a* includes two reagent wells 201 and 202. A liquid first reagent and a liquid second reagent, which need to be lyophilized while being separated from each other, are respectively loaded into two reagent wells 201 and 202, and then a lyophilizing process is performed thereon. As a result, the reagent cartridge 200*a* that includes the reagent well 201 containing the lyophilized first reagent and the reagent well 202 containing the lyophilized second reagent is manufactured. While the FIG. 7 shows a reagent cartridge with two wells, the inventive concept is not limited to such exemplary embodiments. In other embodiments, the reagent cartridge may have three or more wells.

Referring to FIG. 7, the reagent cartridge 200*a* may have a first end 231, a second end 233, a sidewall 232 connected between the first end 231 and the second end 233, and an opening 210 to form two reagent wells 201 and 202. The sidewall may have a partial cylindrical shape as shown in FIG. 7. The surface area of the first end and the surface area of the second end may be the same (e.g., FIG. 7) or different (FIG. 13B). The structures of the reagent cartridge is not critical and may be determined depending on the feasibility or easiness of fabricating them.

Figure 8A:
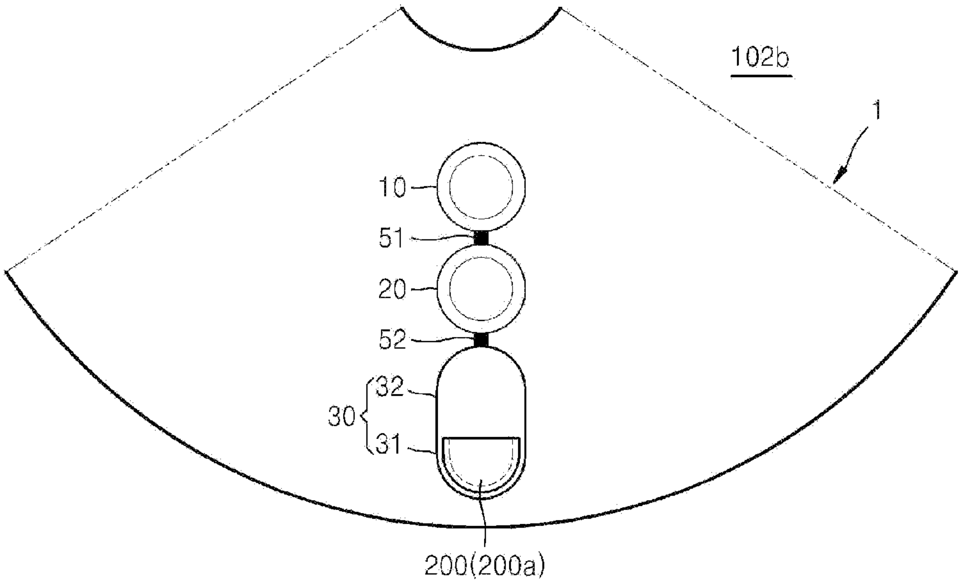
FIG. 8A is a plan view of a microfluidic device according to another embodiment of the present inventive concept, including a disk-type platform.

FIG. 8A is a plan view of a microfluidic device 102*b* according to another embodiment of the present inventive concept, including a disk-type platform. Referring to FIG. 8A, the microfluidic device 102*b* according to the current embodiment is disk-shaped and can be directly mounted on the rotary driving unit 510. Although only a part of the microfluidic device 102*b* is illustrated in FIG. 8A, the platform 1 is circular and disk-shaped. The platform 1 may have the two-layer structure illustrated in FIG. 2 or the three-layer structure illustrated in FIG. 3.

The platform 1 includes a sample chamber 10, a diluent chamber 20, and a detection chamber 30. The detection chamber 30 may be located farther from a rotary center of the platform 1 than the sample chamber 10 and the diluent chamber 20. A valve 51 is formed between the sample chamber 10 and the diluent chamber 20 and a valve 52 is formed between the diluent chamber 20 and the detection chamber 30. A mounting portion 31 of the detection chamber 30 accommodates a reagent cartridge 200 (see FIG. 4) containing a lyophilized reagent or a reagent cartridge 200*a* (see FIG. 7) containing lyophilized reagents.

Figure 8B:
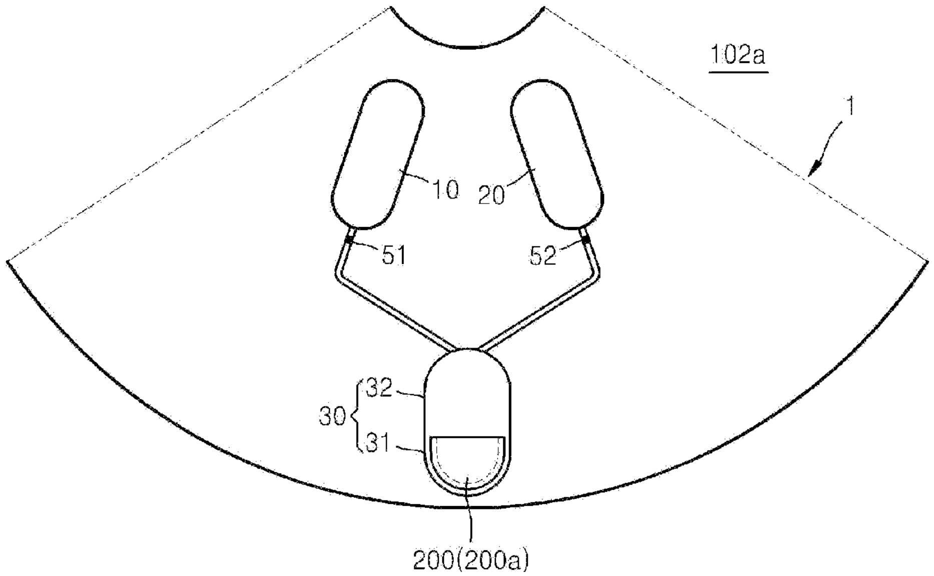
FIG. 8B is a plan view of an exemplary microfluidic device according to another embodiment.

FIG. 8B is a plan view of an example of a modification of the microfluidic device 102*a* of FIG. 8A. In the microfluidic device 102*a* illustrated in FIG. 8B, a sample chamber 10 and a diluent chamber 20 are connected to a detection chamber 30. A valve 51 is formed between the sample chamber 10 and the detection chamber 30 and a valve 52 is formed between the diluent chamber 20 and the detection chamber 30. A reagent cartridge 200 (see FIG. 4) containing a lyophilized reagent or a reagent cartridge 200*a* (see FIG. 7) containing lyophilized reagents is mounted in a mounting portion 31 of the detection chamber 30.

A method of analyzing a sample will now be described in detail. A liquid diluent, such as a buffer or distilled water, is loaded into the diluent chamber 20 of the microfluidic device 102*a* or 102*b*. The sample is loaded into the sample chamber 10. Examples of the sample include, but are not limited to, blood taken from a subject to be examined and a serum separated from the blood.

Then, the microfluidic device 102*a* or 102*b* is mounted on the rotary driving unit 510 of the analyzer (see FIG. 6). The rotary driving unit 110 rotates the microfluidic device 102*a* or 102*b*.

Then, the rotary driving unit 510 rotates in such a way that each of the valves 51 and 52 faces the electromagnetic radiation generator 530. When electromagnetic radiation is irradiated on the valves 51 and 52, a material forming the valve 51 and a material forming the valve 52 melt due to the electromagnetic radiation energy. When the microfluidic device 102*a* or 102*b* is rotated, the sample and the diluent are loaded into the detection chamber 30 by a centrifugal force. The lyophilized reagent, which is contained in the reagent cartridge 200 or 200*a*, is mixed with the sample diluent including the sample and the diluent, and melts. Then, the detection chamber 30, specifically, the detection portion 32 is moved to face the detector 520 to determine whether a material to be detected is present in the reagent mixture in the detection chamber 30, and the amount of the material detected.

Figure 9:
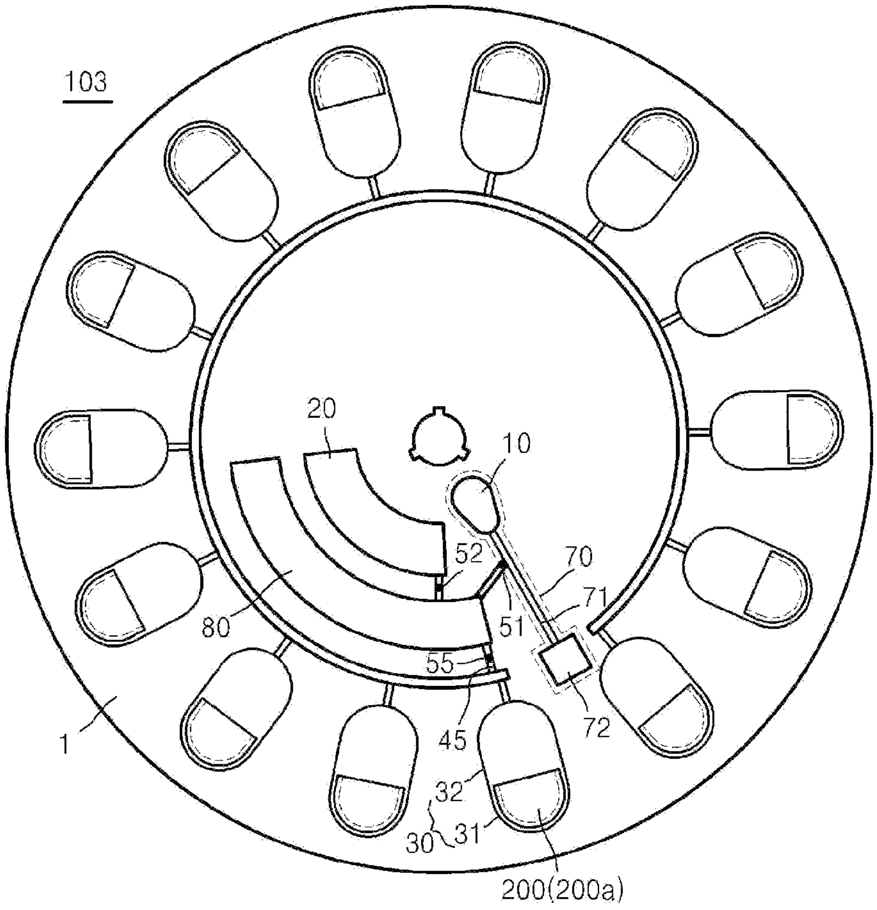
FIG. 9 is a plan view of a microfluidic device according to another embodiment of the present inventive concept, including a centrifuging unit.

FIG. 9 is a plan view of a microfluidic device according to another embodiment of the present inventive concept, including a centrifuging unit. Referring to FIG. 9, the microfluidic device 103 according to the current embodiment is disk-shaped, and can be directly mounted on the rotary driving unit 510 of the analyzer (see FIG. 6). The microfluidic device 103 includes a centrifuging unit 70 for separating a sample into a supernatant and a precipitants. For example, when the sample, which is whole blood, is loaded, the centrifuging unit 70 separates the whole blood into serum (supernatant) and precipitations. The platform 1 is disk-shaped. The platform 1 may have the two-layer structure illustrated in FIG. 2 or the three-layer structure illustrated in FIG. 3.

Hereinafter, a portion of the platform 1 located close to a center of the platform 1 will be referred to as an inner portion (or sometimes referred to as "radially inside"), and a portion of the platform 1 located far from the center will be referred to as an outer portion (or "radially outside"). The sample chamber 10 is closer to the center of the platform 1 than any other element that forms the microfluidic device 103. The centrifuging unit 70 includes a centrifuging portion 71 positioned radially outside the sample chamber 10 and a precipitations collector 72 positioned at an end of the centrifuging portion 71. When a sample is centrifuged, the supernatant remains in the sample chamber 10 or flows to the centrifuging portion 71, and heavy precipitations flow to the precipitations collector 72.

A diluent chamber 20 contains a diluent. The centrifuging portion 71 and the diluent chamber 20 are connected to a mixing chamber 80. A valve 51 is formed between the centrifuging portion 71 and the mixing chamber 80 and a valve 52 is formed between the diluted chamber 20 and the mixing chamber 80.

A plurality of detection chambers 30 are positioned along a circumferential direction of the platform 1. The mixing chamber 80 is connected to the detection chambers 30 by a channel 45. The channel 45 includes a valve 55. The valve 55 may be formed of the same material as that forming the valve 51 and the valve 52. A reagent cartridge 200 or 200*a* containing a lyophilized reagent is mounted on a mounting portion 31 of each of the detection chambers 30. The reagent cartridges 200 or 200*a* may contain the same or different lyophilized reagents.

Figure 11:
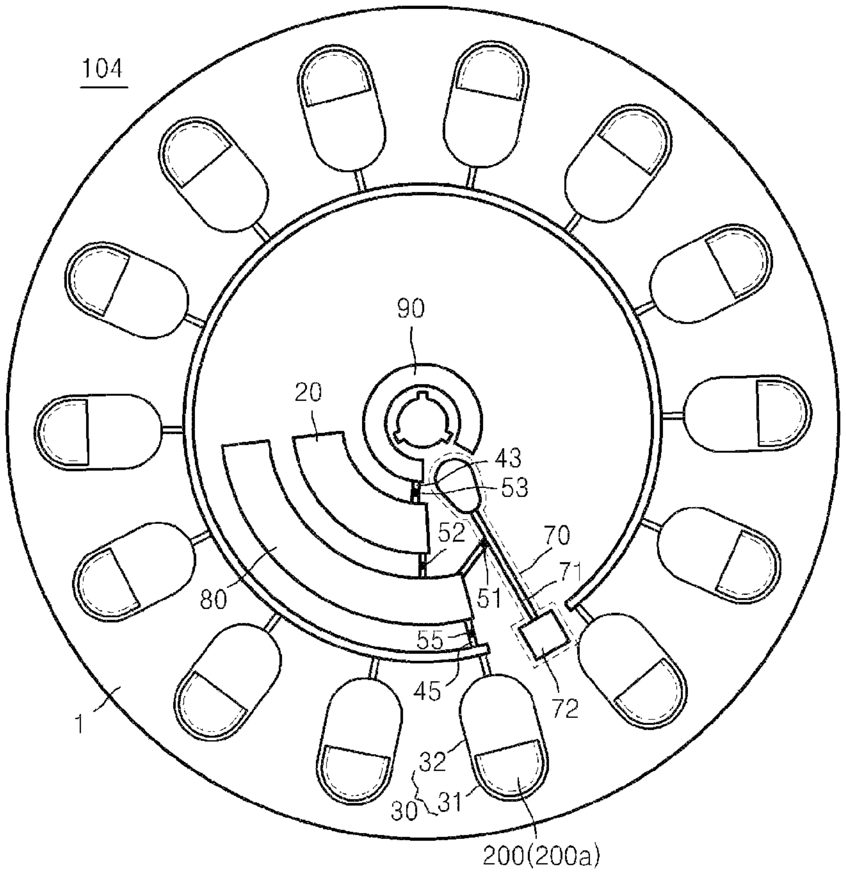
FIG. 11 is a plan view of a microfluidic device according to another embodiment of the present inventive concept, including a container for loading a diluent.
Figure 13G:
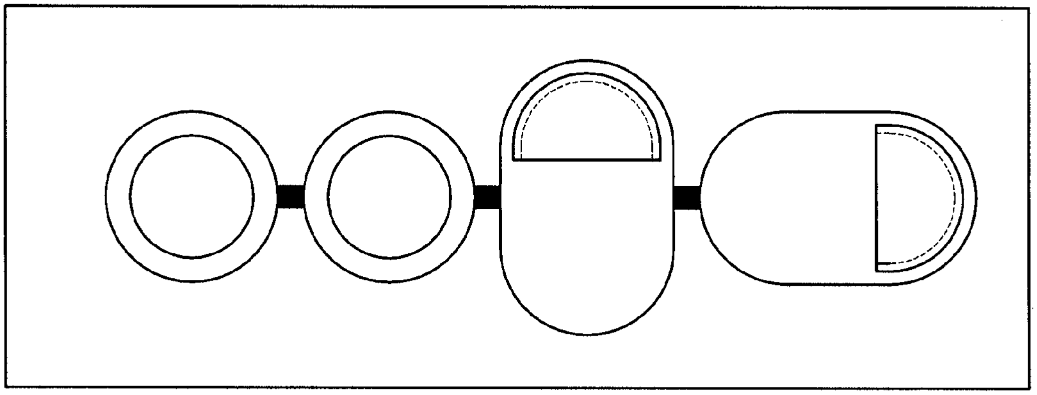
Figure 13H:
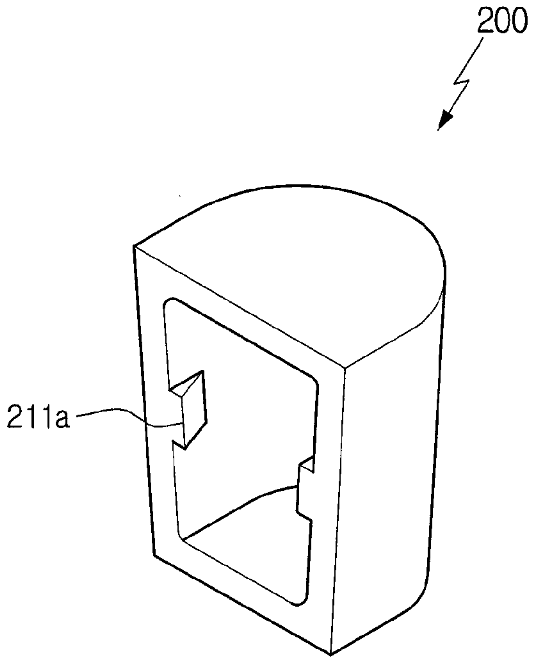
Figure 13I:
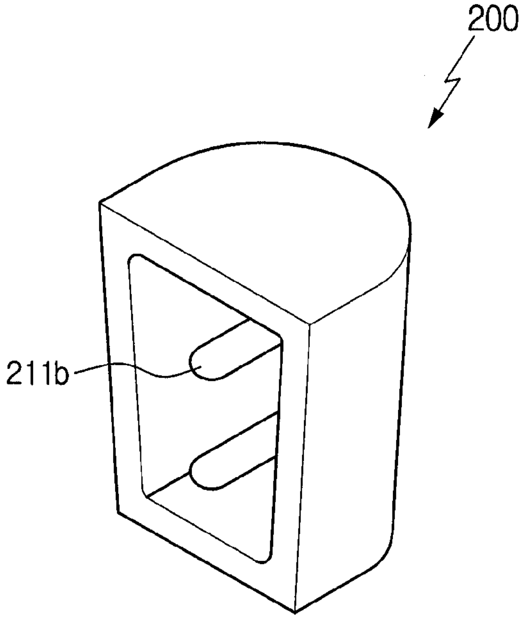
Figure 13J:
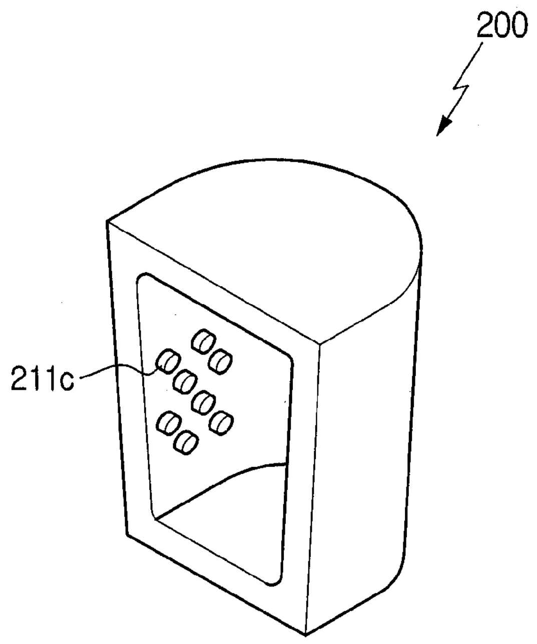
Figure 13K:
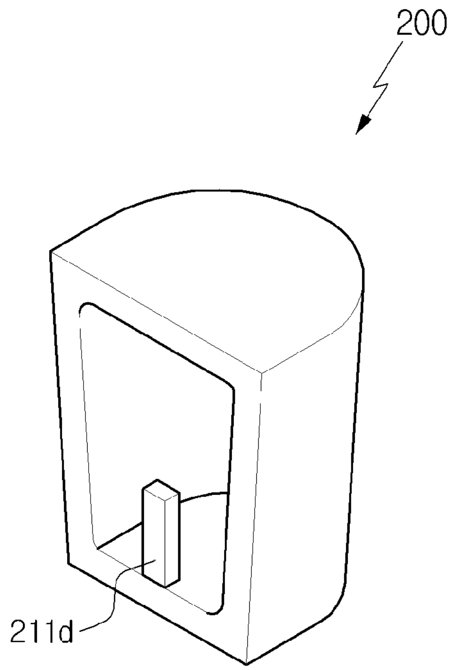

While FIGS. 9 and 11 show plural reagent cartridges are arranged to be parallel connected to a common channel distributing a sample dilutent, the plural reagent cartridges may be serially connected from one to the other, as shown in FIG. 13G. Such arrangement is advantageous when multiple reactions are needed to detect a target component.

A method of analyzing a sample will now be described in detail. A liquid diluent, such as a buffer or distilled water, is loaded into the diluent chamber 20 of the microfluidic device 103 of the diluent chamber 20. The sample is loaded into the sample chamber 10. Examples of the sample include blood taken from a subject to be examined and a serum separated from the blood.

Then, the microfluidic device 103 is mounted on the rotary driving unit 510 of the analyzer (see FIG. 6). The rotary driving unit 110 rotates the microfluidic device 103. As a result, due to a centrifugal force, the supernatant of the sample contained in the sample chamber 10 remains in the sample chamber 10 or flows to the centrifuging portion 71, and relatively heavy precipitations of the sample contained in the sample chamber 10 flow to the precipitations collector 72.

Then, the rotary driving unit 510 moves the microfluidic device 103 so that the valves 51 and 52 face the electromagnetic radiation generator 530. When electromagnetic radiation is irradiated on the valves 51 and 52, a valve forming material that forms the valves 51 and 52 melts due to electromagnetic radiation energy. When the microfluidic device 106 is rotated, the sample and the diluent are loaded into the mixing chamber 80, thereby forming a diluent sample including the sample and the diluent in the mixing chamber 80. To mix the sample with the diluent, the rotary driving unit 510 may laterally shake the microfluidic device 103 a few times.

Then, the rotary driving unit 510 moves the microfluidic device 103 so that the valve 55 faces the electromagnetic radiation generator 530. When electromagnetic radiation is irradiated on the valve 55, a valve forming material that forms the valve 55 melts due to the electromagnetic radiation energy and the channel 45 is opened. When the microfluidic device 103 rotates, the diluted sample is loaded into the detection chamber 30 through the channel 45. The lyophilized reagent is mixed with the diluent sample and melts, thereby forming a reagent mixture. To dissolve the lyophilized reagent, the rotary driving unit 510 may move the microfluidic device 103 a few times in a reciprocal motion.

Then, the detection chamber 30 is moved to face the detector 520 so as to identify whether a target material to be detected is present in the reagent mixture in the detection chamber 30, and to measure the amount of the detected material, thereby completing the sample analysis.

Figure 10:
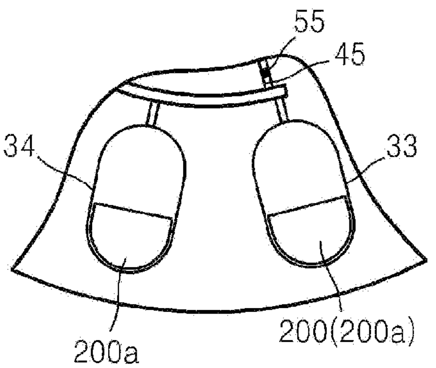
FIG. 10 is a view to explain a detection operation including multi-step reactions using the microfluidic device of FIG. 9.

Hereinafter, a detection process including 2-step reactions, such as a process of detecting HDL from a sample, will be described with reference to the microfluidic device 103 illustrated in FIG. 9. In this case, as illustrated in FIG. 10, a first-reagent cartridge 200 or 200*a* containing a first reagent is mounted on a first detection chamber 33, and a second-reagent cartridge 200*a* containing a first reagent and a second reagent is mounted on a second detection chamber 34. The first reagent and the second reagent have components as described below.

| <First reagent> | |
|---|---|
| Piperazine-1,4-bis(2-ethanesulfonic acid) (PIPES): | 30 MMOL/L |
| 4-Aminoantipyrine (4-AAP): | 0.9 MMOL/L |
| Peroxidase (POD): | 240 Unit/L |
| Ascorbic oxidase (ASOD): | 2700 Unit/L |
| Anti human b-lipoprotein antibody | |
| **<Second reagent>** | |
| Piperazine-1,4-bis(2-ethanesulfonic acid) (PIPES): | 30 MMOL/L |
| Cholesterol esterase (CHE): | 4000 U/L |
| Cholesterol oxidase (COD): | 20000 U/L |
| N-(2-hydroxy-3-sulfopropyl)-3.5-dimethoxyaniline (H-DASO): | 0.8 MMOL/L |

In the first detection chamber 33, the first reagent is mixed with the diluted sample and left to sit at about 37° C. for 5 minutes. As a result, HDL, LDL, very low density lipoprotein (VLDL), and chylomicron are formed into soluble HDL, and then soluble HDL is decomposed into cholesterol and hydrogen peroxide. The hydrogen peroxide is decomposed into water and oxygen.

In the second detection chamber 34, the first reagent, the second reagent, and the diluted sample are mixed together, and left to sit at about 37° C. for 5 minutes. As a result, HDL, LDL, VLDL, and chylomicron are formed into soluble HDL due to an enzyme reaction caused by the first reagent, and the soluble HDL is decomposed into cholestenone and hydrogen peroxide. The hydrogen peroxide is decomposed into water and oxygen. The residual HDL forms a pigment through an enzyme reaction with the second reagent. Absorbance of the first and second detection chambers 33 and 34 was measured by irradiating light thereon using the detector 520 (see FIG. 6).

Based on the two results of measuring the absorbance, it can be identified whether HDL is present and the amount of HDL can be calculated.

Figure 12A:
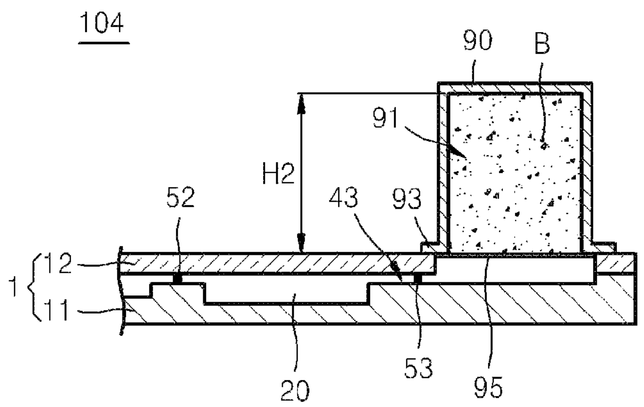
FIGS. 12A and 12B are sectional views of the microfluidic device of FIG. 11.
Figure 12B:
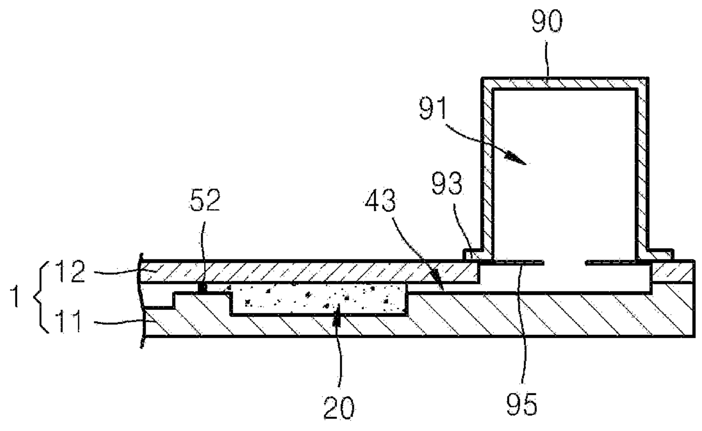

FIG. 11 is a plan view of a microfluidic device 104 according to another embodiment of the present inventive concept, including a container 90 for loading a diluent. FIGS. 12A and 12B are sectional views of the microfluidic device 104 of FIG. 1. The microfluidic device 104 according to the current embodiment is different from the microfluidic device 103 of FIG. 9, in that a container 90 containing a diluent is coupled to the platform 1 and the container 90 is connected to the diluent chamber 20 by a channel 43. The channel 43 may include a valve 53. The valve 53 may be formed of the same material as that forming the valves 51 and 52. However, in some embodiments, the channel 43 may not include the valve 53 because flow of the diluent is controlled by a membrane 95.

Referring to FIGS. 11, 12A, and 12B, the platform 1 includes a top plate 12 and a bottom plate 11 coupled to the top plate 12. The container 90 includes a housing space 91 for housing a diluent. The container 90 may be formed by, for example, injection-molding a thermoplastic resin, and is fixed on the platform 1. The housing space 91 is sealed by the membrane 95. The container 90 is turned upside down and the housing space 91 is filled with a diluent, and then the lid 95 is attached to an opening 93 of the container 90 so as to prevent leakage of the diluent. A fluid pouch that contains the diluent may be located inside the container 90, and the fluid pouch can be destroyed and sealed.

The membrane 95 is an example of a control member that controls flow of the diluent from the container 90 to the channel 43. The membrane 95 prevents leakage of the diluent contained in the housing space 91. The membrane 95 may be destroyed or melted by electromagnetic radiation energy of, for example, a laser ray.

For example, the membrane 95 may include a thin layer and an electromagnetic radiation absorption layer formed thereon. The thin layer may be formed of metal. The electromagnetic radiation absorption layer may be formed by a coating of an electromagnetic radiation absorbing material. Due to the electromagnetic radiation absorption layer, the membrane 95 absorbs external electromagnetic radiation and is destroyed or melted. The thin layer may be formed of, in addition to metal, any material that is destroyed or melted when exposed to electromagnetic radiation. In this regard, the thin layer may be formed of a polymer. A portion of the container 90 is transparent so that externally projected electromagnetic radiation passes through the container 90 and reaches the membrane 95.

The microfluidic device 104 is mounted on the rotary driving unit 510 of the analyzer (see FIG. 6), and electromagnetic radiation is projected on the membrane 95 for a selected time period using the electromagnetic radiation generator 530 (see FIG. 6). As a result, as illustrated in FIG. 12B, the membrane 95 is destroyed or melted.

Then, electromagnetic radiation is projected on the valve 53 for a selected time period using the electromagnetic radiation generator 530 (see FIG. 6). As a result, a material for forming the valve 53 melts and the channel 43 opens. The diluent contained in the housing space 91 flows to the diluent chamber 20 through the channel 43. Then, an analysis process is performed in the same manner as described with reference to the microfluidic device 103 of FIG. 9.

As described above, a microfluidic device according to the embodiments of the present inventive concept can be manufactured without a great amount of effort to simultaneously form small and accurately volume-controlled lyophilized reagent beads, and without any difficulty for loading lyophilized reagent beads into the microfluidic device. In addition, since an accurate amount of a liquid reagent is loaded into a reagent cartridge that is smaller than the microfluidic device and then the loaded liquid reagent is lyophilized, a reagent cartridge in which an accurate amount of lyophilized reagent is contained can easily be mass-produced. Accordingly, since a microfluidic device in which an accurate amount of lyophilized reagent is contained in advance can be mass-produced, the manufacturing costs are low and high compatibility can be achieved.

While aspects of the present invention have been particularly shown and described with reference to differing embodiments thereof, it should be understood that these exemplary embodiments should be considered in a descriptive sense only and not for purposes of limitation. Descriptions of features or aspects within each embodiment should typically be considered as available for other similar features or aspects in the remaining embodiments.

Thus, although a few embodiments have been shown and described, it would be appreciated by those of ordinary skill in the art that changes may be made in these embodiments without departing from the principles and spirit of the invention, the scope of which is defined in the claims and their equivalents.

What is claimed is:

1. A microfluidic device comprising:

a platform including a chamber containing a fluid; and a reagent cartridge mounted to the platform, the reagent cartridge comprising a closed first end, a closed second end, a sidewall connecting the first end and the second end, an opening formed in the sidewall, and a well containing a solid reagent for detecting a material contained in the fluid, wherein the platform includes at least one detection chamber in which the reagent cartridge is mounted.

2. The microfluidic device of claim 1, wherein the solid reagent is a lyophilized solid reagent.

3. The microfluidic device of claim 1, wherein the microfluidic device comprises at least two reagent cartridges each containing the same or different lyophilized reagents from the other.

4. The microfluidic device of claim 1, wherein the reagent cartridge comprises a plurality of reagent wells each containing a different reagent.

5. The microfluidic device of claim 1, wherein at least part of the detection chamber is made of a transparent material and the at least part of the detection chamber is the part not housing the reagent cartridge.

6. The microfluidic device of claim 5, wherein the reagent cartridge is mounted in the detection chamber in such a way that the opening of the reagent cartridge faces the fluid flowing into the detection chamber.

7. The microfluidic device of claim 1, wherein the platform comprises:

a sample chamber to accommodate the sample;

a diluent chamber to accommodate a diluent; and a valve for controlling the flow of the fluid disposed at at least one point between said chambers.

8. The microfluidic device of claim 7, wherein the valve is controlled according to pressure of the fluid.

9. The microfluidic device of claim 8, wherein the pressure is generated when the microfluidic device rotates.

10. The microfluidic device of claim 7, wherein the valve is formed of a valve forming material that opens by electromagnetic radiation energy.

11. The microfluidic device of claim 10, wherein the valve forming material is selected from a phase transition material and a thermoplastic resin, wherein the phase of the phase transition material or the thermoplastic resin changes by electromagnetic radiation energy.

12. The microfluidic device of claim 10, wherein the valve forming material comprises micro heat-dissipating particles which are dispersed in a phase transition material, absorb the electromagnetic radiation energy, and dissipate the energy.

13. The microfluidic device of claim 7, further comprising a container coupled to the platform and providing the diluent to the diluent chamber.

14. The microfluidic device of claim 1, wherein the solid reagent comprises at least one reagent selected from the group consisting of reagents for detecting serum, aspartate aminotransferase (AST), albumin (ALB), alkaline phosphatase (ALP), alanine aminotransferase (ALT), amylase (AMY), urea nitrogen (BUN), calcium ($Ca^{++}$), total cholesterol (CHOL), creatine kinase (CK), chloride ($Cl^-$), creatinine (CREA), direct bilirubin (D-BIL), gamma glutamyl transferase (GGT), glucose (GLU), high-density lipoprotein cholesterol (HDL), potassium ($K^+$), lactate dehydrogenase (LDH), low-density lipoprotein cholesterol (LDL), magnesium (Mg), phosphorus (PHOS), sodium ($Na^+$), total carbon dioxide ($TCO_2$), total bilirubin (T-BIL), triglycerides (TRIG), uric acid (UA), and total protein (TP).

15. The microfluidic device of claim 14, wherein the solid reagent comprises an additive.

16. The microfluidic device of claim 15, wherein the additive is a filler that comprises at least one material selected from the group consisting of bovine serum albumin (BSA), polyethylene glycol (PEG), dextran, mannitol, polyalcohol, myo-inositol, an citric acid, ethylene diamine tetra acetic acid disodium salt (EDTA2Na), and polyoxyethylene glycol dodecyl ether (BRIJ-35).

17. The microfluidic device of claim 15, wherein the additive is a surfactant that comprises at least one material selected from the group consisting of polyoxyethylene, lauryl ether, octoxynol, polyethylene alkyl alcohol, nonylphenol polyethylene glycol ether; ethylene oxide, ethoxylated tridecyl alcohol, polyoxyethylene nonylphenyl ether phosphate sodium salt, and sodium dodecyl sulfate.

18. The microfluidic device of claim 1, wherein at least a portion of a shape of the solid reagent is complementary to at least a portion of an inner configuration of the well of the reagent cartridge.

19. The microfluidic device of claim 7, wherein the detection chamber comprises a structure preventing the reagent cartridge from freely moving within the detection chamber.

20. The microfluidic device of claim 1, wherein the well of the reagent cartridge comprises a structure increasing retention of the solid reagent in the reagent cartridge.

21. A microfluidic device comprising:

a platform comprising a chamber and channels;

a reagent cartridge housed in the chamber, the reagent cartridge comprising a closed first end, a closed second end, a sidewall connecting the first end and the second end, and an opening formed in the sidewall to form a well; and a soluble solid reagent accommodated in the well of the reagent cartridge, wherein the reagent cartridge is mounted within the chamber and wherein the well of the reagent cartridge is in fluid communication with the chamber.

22. The microfluidic device according to claim 21, wherein the reagent cartridge is fitted into the chamber.

23. The microfluidic device according to claim 21, wherein the microfluidic device comprises a first chamber housing a first reagent cartridge and a second chamber housing a second reagent cartridge;

wherein the first reagent cartridge contains a first reagent;

wherein the second reagent cartridge contains a second reagent; and the first reagent and the second reagent are the same or different.

24. The microfluidic device according to claim 23, wherein the first reagent and the second reagent are different from each other; and wherein the first chamber receives fluid which contacts the first reagent contained in the first reagent cartridge to form a first reaction mixture and the second chamber receives the first reaction mixture which contacts the second reagent contained in the second reagent cartridge to form a second reaction mixture.

25. The microfluidic device according to claim 21, wherein the reagent cartridge comprises at least two wells each accommodating a reagent.

26. The microfluidic device according to claim 21, wherein the well of the reagent cartridge comprises a structure to retain the reagent accommodated in the reagent cartridge.

27. The microfluidic device according to claim 26, wherein the structure is at least one protrusion formed inside the well.

28. The microfluidic device according to claim 21, wherein the chamber has an indentation retaining the reagent cartridge in the chamber.

29. The microfluidic device according to claim 21, wherein the chamber comprises a protrusion to hold the reagent cartridge in the chamber.

30. A cartridge adapted to be installed in a microfluidic device, the cartridge comprising:

a body including a first end, a second end, a sidewall connected to the first end and to the second end, and an opening formed in the sidewall to form a well in the body; and a solid reagent contained in the well in a unit usage amount, wherein the body is mounted within a chamber of the microfluidic device and wherein the well is in fluid communication with the chamber.

31. The cartridge according to claim 30, wherein a shape of at least one portion of the reagent is complementary to a portion of an internal shape of well.

32. The cartridge of claim 30, wherein the body comprises at least two wells each containing a solid reagent.

33. The cartridge of claim 30, further comprising a structure provided in the well to retain the solid reagent accommodated therein.

34. The cartridge of claim 33, wherein the structure is at least one protrusion formed inside the well.

35. A cartridge suitable for a microfluidic device, comprising:

a body including a closed first end, a closed second end, a closed wall connecting the first and second ends, an opening formed in the wall, and a well accessible through the opening; and a solid reagent contained in the well, wherein the body is mounted within a chamber of the microfluidic device and wherein the well is in fluid communication with the chamber.

* * * * *